United States Patent [19]
Gouda et al.

[11] Patent Number: 5,902,798
[45] Date of Patent: May 11, 1999

[54] METHOD OF PROMOTING DERMAL WOUND HEALING WITH CHITOSAN AND HEPARIN OR HEPARIN SULFATE

[75] Inventors: Ibrahim Gouda, Sollentuna; Olle Larm, Bromma, both of Sweden

[73] Assignee: Medicarb AB, Bromma, Sweden

[21] Appl. No.: 08/765,353

[22] PCT Filed: Jul. 18, 1995

[86] PCT No.: PCT/SE95/00875

§ 371 Date: Dec. 31, 1996

§ 102(e) Date: Dec. 31, 1996

[87] PCT Pub. No.: WO96/02260

PCT Pub. Date: Feb. 1, 1996

[30] Foreign Application Priority Data

Jul. 19, 1994 [SE] Sweden ................................ 9402531

[51] Int. Cl.⁶ ........................ A61K 31/73; A61K 31/725; A61K 35/56
[52] U.S. Cl. ................................ 514/55; 514/54; 514/56; 514/59; 514/57; 424/538; 536/20; 536/21
[58] Field of Search ................................ 514/54, 56, 57, 514/59, 55; 536/20, 21; 424/538

[56] References Cited

U.S. PATENT DOCUMENTS

| | | | |
|---|---|---|---|
| 4,326,532 | 4/1982 | Hammar | 604/266 |
| 4,378,017 | 3/1983 | Kosugi et al. | 424/499 |
| 4,532,134 | 7/1985 | Malette et al. | 514/55 |
| 4,572,906 | 2/1986 | Sparkes et al. | 514/21 |
| 4,879,282 | 11/1989 | Saliba, Jr. | 514/56 |
| 5,002,582 | 3/1991 | Guire et al. | 623/66 |
| 5,037,810 | 8/1991 | Saliba, Jr. | 514/56 |
| 5,116,824 | 5/1992 | Miyata et al. | 514/55 |

FOREIGN PATENT DOCUMENTS

| | | |
|---|---|---|
| 1202904 | 4/1986 | Canada . |
| 0051354 | 5/1982 | European Pat. Off. . |
| 6-24934 | 2/1994 | Japan . |
| WO88/06840 | 9/1988 | WIPO . |
| WO 96/02258 | 2/1996 | WIPO . |

OTHER PUBLICATIONS

Saliba, Jr., et al., JAMA, 225:261–269, 1973.

Journal of Periodontology, vol. 62, No. 10, 1991, S. Pitaru et al., "Heparan Sulfate and Fibronectin Improve the Capacity of Collagen Barriers to Prevent Apical Migration of the Junctional Epithelium", p. 598.

Biomaterials, vol. 14, No. 12, 1993, R.A.A. Muzzarelli et al., "Osteoconductive properties of methylpyrrolidinone chitosan in an animal model", p. 925.

Department of Histology, vol. 64, 1989, L. Peter Nilsson, "Effects of Hyperbaric Oxygen Treatment on Bone Healing", pp. 19–20.

*Primary Examiner*—David M. Naff
*Assistant Examiner*—Janet M. Kerr
*Attorney, Agent, or Firm*—Burns, Doane, Swecker & Mathis, L.L.P.

[57] ABSTRACT

The invention relates to a method for promoting the healing of dermal wounds by applying a composition containing chitosan and the polysaccharide, heparin or heparan sulfate. Heparin or heparan sulfate can be immobilized to chitosan by ionic or covalent bonds, and the degree of N-acetylation of chitosan can range from 25% to 90%. The composition can include a cellulose derivative as an additional polysaccharide to increase the viscosity of the composition. The combination of chitosan and polysaccharide, when applied to a wound site, effectively stimulates and accelerates wound healing.

15 Claims, 2 Drawing Sheets

METHOD OF PROMOTING DERMAL WOUND HEALING WITH CHITOSAN AND HEPARIN OR HEPARIN SULFATE

TECHNICAL AREA

The present invention relates to new agents to accelerate, stimulate or promote the healing of dermal wounds. The invention also includes a process for the treatment of dermal wounds.

BACKGROUND OF THE INVENTION

With regard to wound ointments and similar agents for the treatment of dermal wounds, i.e. disorders in the form of wounds in the epidermis arising through accident, surgical incision or without exterior influence, for example wounds in connection with acne, so called chaps or the like, the market is flooded by products of different kinds. These products are characterized by containing as active constituents active substances of different kinds, for example antibiotics, antiinflammatory etc. whose action primarily is not directed to stimulate healing but instead are directed to act as desinfectants or in some other manner perform a cleaning action. The components contained are therefore often of such a character that they are not biodegradable to a desired degree, the storage stability also leaving something to be desired. Therefore, for the purpose of improving storage stability known products for dermal treatment often contain one or several excipients to prevent or delay decomposition, and among such excipients there may be mentioned sodium disulphate, dithiotreitol and others.

SUMMARY OF THE INVENTION

The present invention has for an object to provide agents which accelerate, stimulate or promote healing of dermal wounds.

Another object of the invention is to provide such an agent, at whose use no inflammatory response will arise.

Yet another object of the invention is to provide agents which are bioacceptable and biodegradable without giving raise to deleterious decomposition products.

A further object of the invention is to provide a process for the treatment of dermal wounds.

For these and other objects which will be clear from the following disclosures there is provided by the present invention a new use of chitosan in combination with a first polysaccharide selected from heparin, heparan sulfate and dextran sulfate for the manufacture of an agent that accelerates, stimulates and/or promotes healing of dermal wounds.

In the present context the expression "dermal wound" is intended to cover any disorder in association with dermis in the form of regular wounds arising through accident, surgical incision or in another manner by exterior influence, or wounds which have arisen without exterior influence, such as acne, so called chaps or other fissures in the dermis.

The first polysaccharide used can be present in the agent in admixture with a chitosan and possible other ingredients, but can also be immobilized to the chitosan in three different ways. Immobilization can thus take place by ionic bond, by covalent bond or by mechanical inclusion in the chitosan in connection with its precipitation from a solution. A process for the covalent binding of the relevant polysaccharide to a substrate carrying amino groups, which substrate can be constituted by chitosan is described in U.S. Pat. No. 4,613,665.

As a polysaccharide it is particularly preferred to use heparin or heparan sulfate, both of which are commercially available on the market from several manufacturers. Also partially hydrolyzed forms of the polysaccharide can, of course, also be used provided that the biological activity is maintained.

The agent for healing of dermal wounds involved in the present invention can be presented in different physical forms, for example as powders, ointments, pastes, gels, suspensions or solutions. The form used is, of course, adapted to the dermal disorder to be treated. For certain types of wound treatment the treatment agent according to the invention may also be presented in the form of thin films or membranes.

One of the main components in the subject treatment agent for dermal wounds is thus chitosan which is a linear 1,4-bound polysaccharide built up from β-D-glucose amine entities. The chitosan is manufactured by N-deacetylation of chitin, a polymer forming the shell of inter alia insects and crayfish. Commercial chitin is recovered from crab and shrimp shell which are waste products from the fishing industry. By controlling the alkali treatment of chitins it is possible to manufacture chitosans of varying degrees of N-acetylation. When treating chitin with alkali, usually sodium hydroxide, N-deacetylation thus takes place, i.e. acetamido groups are converted to amino groups to form chitosan.

The physical properties of chitosan affecting its utility depend on the degree of N-acetylation, molecular weight and homogeneity. The chitosan is biodegradable, both by chitinas from the digestive system and by lysozyme in body fluids.

It is preferred in connection with the use of the present invention that the chitosan has a degree of N-acetylation of at most about 90% and preferably at most about 50%. It is particularly preferred that the degree of N-acetylation is less that about 25%.

The two main components of the wound treatment agent, the chitosan and the first polysaccharide, particularly heparin or heparan sulfate, are suitably used in combination with a conventional carrier or excipient of an acceptable character. Quite generally it is preferred that the matrix is an aqueous matrix, the carrier or the excipient containing a viscosity increasing second polysaccharide, which can be selected from hemicelluloses, for example arabino xylanes and glukomannanes, plant gums, for example guar gum, locust bean gum, celluloses and derivatives thereof, for example methyl cellulose, ethyl cellulose, hydroxi ethyl cellulose, carboxi methyl cellulose, starch and starch derivatives, for example hydroxi ethyl starch or crosslinked starch, microbial polysaccharides, for example xanthan gum, curdlan, pullulan, dextran. Also algi polysaccharides, for example agar, carrageenans, alginic acid, can be used as a constituent in the carrier or excipient.

A preferred second polysaccharide is a cellulose derivative, for example methyl cellulose.

It is preferred that said first polysaccharide is heparin or heparan sulphate. It is furthermore preferred that said first polysaccharide is present in the composition in an amount of at least about 2% by weight based on the combined amount of polysaccharide and chitosan in the composition. It is particularly preferred that said amount is at least about 4% by weight and preferably at least about 6% by weight. The upper limit as to said amount is not particularly critical, but for economic reasons it is preferred to use no more than about 10% by weight of said first polysaccharide, particularly since higher amounts thereof do not increase the degree of re-epithelialisation.

The present invention also provides a process for the acceleration, stimulation or promotion of healing in connection with the treatment of dermal wounds. This process means that at the location there is topically applied an agent comprising chitosan in combination with a first polysaccharide selected from heparin, heparan sulphate and dextran sulphate.

Said first polysaccharide in connection with such process is preferably heparin or heparan sulphate. The agent is suitably applied in the form of a powder, an ointment, a paste, a gel, a suspension, a solution or a film.

BRIEF DESCRIPTION OF THE FIGURES

The present invention will in the following be illustrated in connection with non-limiting examples. In said examples parts and percentages refer to weight if not otherwise stated. This illustration is made in association with the appended drawings, wherein.

EXAMPLES OF PREFERRED EMBODIMENTS

Example 1

Coupling of Heparin to Crosslinked Starch

Figure 1:
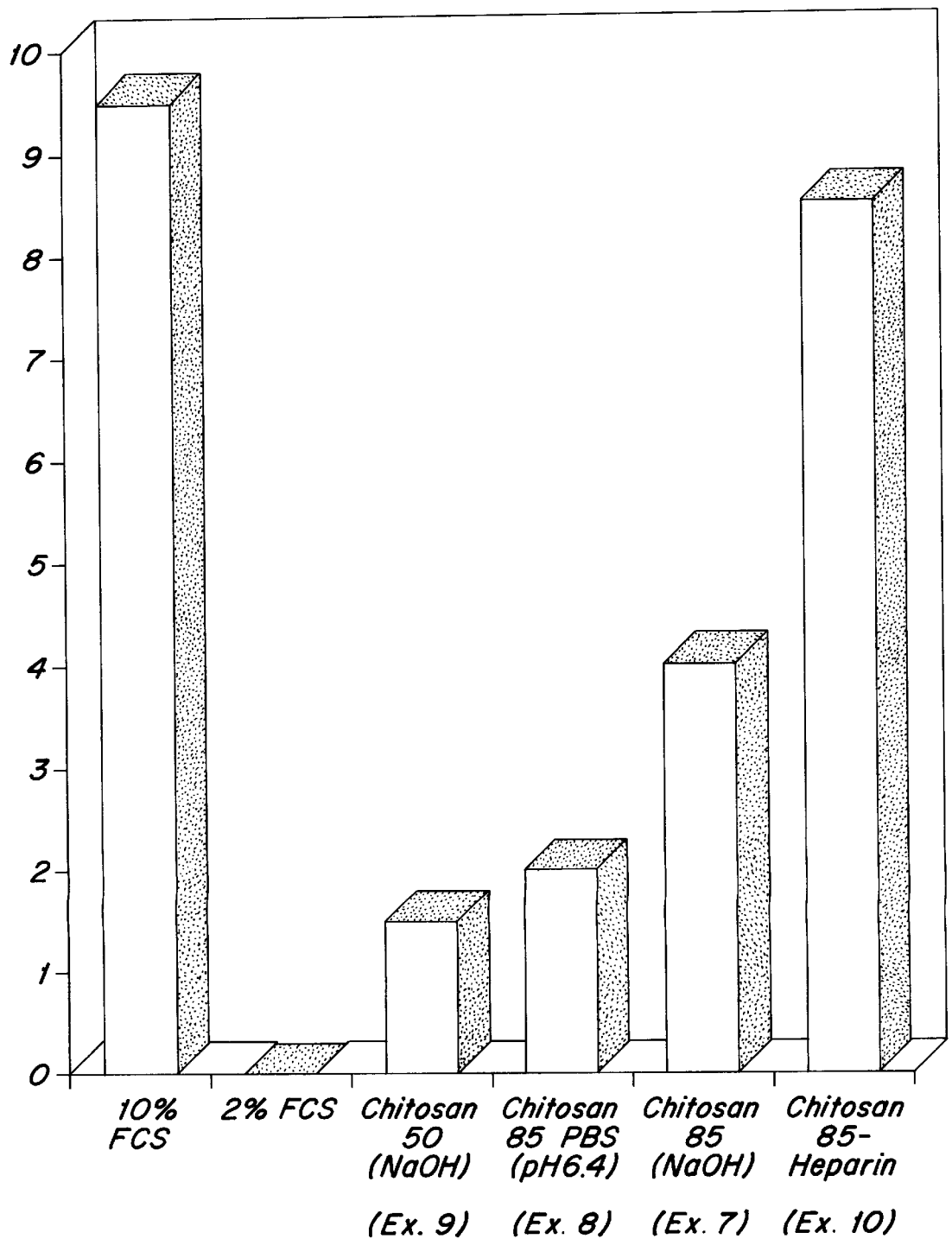
FIG. 1 is a diagram showing the degree of healing as a function of different substances and products used in the experiments.

Microspheres of crosslinked starch (Eldexomer, Perstorp) are subjected to periodate oxidation. 25 g eldexomer is slurried in 1 L of water. 2.5 g sodium periodate are added and the reaction mixture is allowed to stand under shaking over night. The gel-formed material is filtered off and washed with water.

5 g of the periodate oxidated gel is transferred to 500 ml chitosan solution (0.25% w/v of 85% degree of deacetylation) together with 200 mg sodium cyanoboro hydride. Under shaking the solution is allowed to stand over night at room temperature. The gel is then washed with water and an indication test with regard to amino groups is carried out.

250 mg of nitrite degraded heparin is dissolved in 500 ml distilled water together with 4.4 g sodium chloride. The pH is adjusted to 3,9 using dilute hydrochloric acid, and 10 mg of sodium cyanoboro hydride are added. The starch gel prepared according to the above is added to the heparin solution. Incubation under shaking takes place over night, the gel being then washed with water.

Example 2

Heparinized Chitosan Pearls

A solution (2% w/v) of chitosan of 84% degree of deacetylation (Pronova Biopolymers, Seacure Cl 313) is pumped dropwise through a capillary (inner diameter 0.8 mm) down into a sodium phosphate buffer, 0.1 M, pH 7, 250 mL. Gel pearls of chitosan having a diameter of 1.2 mm are formed.

Heparin (Pig mucosa, Kabivitrum) is added to the buffer solution to a concentration of about 1 mg/mL, the heparin being ionbound to the chitosan pearls. After filtration on a glass filter funnel and drying the diameter of the pearls is reduced to about 0.8 mm. The pearls obtained are then pressed and used as a paste in dermal applications.

Example 3

Chitosan Film with Heparinized Surface 2 g chitosan having a degree of deacetylation of 84% are dissolved in 200 mL sterile filtered distilled water. The films are prepared by transferring the chitosan solution obtained to petridishes of 54 $cm^2$ with 20 mL chitosan solution in each dish. Evaporation and drying at 70° C. for 16 h results in the formation of a film having an approximate thickness of 0.1 mm.

1 g heparin (Pig mucosa, Kabivitrum) is dissolved in 100 mL sterile filtered phosphate buffer, pH 6.4. 20 mL of the solution obtained are added to each petridish containing the chitosan film prepared. The dish is subjected to shaking over night. This neutralizes the film at the same time as heparin is ionbound to its surface. Next day the films are washed with sterile filtered distilled water and allowed to dry at room temperature.

Example 4

Preparation of Ointment

An ointment is prepared containing the following constituents:
0.5% methyl cellulose
1% chitosan (Seacure Cl 211, 57% degree deacetylation)
0.2% heparin (Pig mucosa, Kabivitrum)
2% glycerol,
plus water, adjustment of pH of 5.6.

The ointment is prepared by admixing 100 mL chitosan (2% w/v) in a turnmixer with 50 mL methyl cellulose (1% w/v). 400 mg heparin are dissolved in 50 mL distilled water and this solution is then admixed into the turn-mixer with the solution of chitosan and methyl cellulose. Finally, 4 mL of glycerol are added under continued stirring.

The ointment obtained has a highly viscous consistency and is found to be very effective for the treatment of so called juvenile acne.

Example 5

Preparation of Wound Powder

A wound powder is prepared by mixing chitosan powder (Seacure Cl 210, 82% degree of deacetylation, Pronova Biopolymer) heparin (Pig mucosa, Kabivitrum) and microspheres of crosslinked starch (Eldexomer, Perstorp) in the proportions 9:1:90. The powder obtained can be directly applied to dermal wounds and then preferably coated with a dressing or adhesive.

Example 6

Preparation of Chitosan Film 2 g of hydrochloride salt of chitosan (Seacure Cl 313, 84% degree of deacetylation, Pronova Biopolymer) are dissolved in 200 mL of sterile filtered distilled water. The films are prepared in petridishes of 54 $cm^2$, 20 mL of the chitosan solution prepared being added to each dish, and evaporation and drying then takes place at 70° C. for 16 h. The films obtained are then subjected to varying treatment.

Example 7

Neutralization of Film Using Sodium Hydroxide to each petridish containing the film prepared according to Example 6 there are added 20 mL sterile filtered 1 M NaOH.

After about 3 h the films are rinsed with sterile filtered distilled water to neutral pH. The films are dried at room temperature and then packed into sterile bags. Autoclavation for 30 min takes place at 125° C. for sterilization.

Example 8

Neutralization of Film in Phosphate Buffer

To each petridish containing film prepared according to Example 6 there are added 20 mL sterile filtered phosphate buffer 0.2 M, pH 6.4. After about 3 h the films are rinsed with sterile filtered distilled water and are then allowed to dry at room temperature. They are then packed in sterile bags and autoclaved in accordance with Example 7.

Example 9

Preparation of Alternative Chitosan Film

Example 6 is repeated but using chitosan having 57% degree of deacetylation (Seacure Cl211, Pronova Biopolymer). The films obtained are then neutralized with NaOH in accordance with Example 7.

Example 10

Heparinization of Chitosan Film 1 g of heparin (Pig mucosa, Kabivitrum) is dissolved in 100 mL sterile filtered phosphate buffer 0.2 M, pH 6.4. 20 mL of the solution obtained are then added to each petridish containing chitosan film prepared in accordance with Example 6. The petridishes are subjected to slow shaking over night, the films being neutralized at the same time as heparin is ionbound to the surface of the films.

The next day the films are washed with sterile filtered distilled water and are then allowed to dry at room temperature. The films are packed in sterile bags with the heparinized surface facing upwardly and are then autoclaved for 30 min at 125° C. for sterilization.

Example 11

Test in Vitro of Wound Healing

Sterile humane skin is obtained from routine breast operations for the reduction of breast size. Under sterile conditions pieces having a diameter of 6 mm are cut with a biopsy punch. In the centre of each piece there is provided on the epidermal side a non-through wound with a 3 mm biopsy punch, and the pieces are then transferred to plates with 24 wells. Each wound is then covered with the test substance, in the present case fetal calf serum, 10%, 2% and the products from Example 7–10 above. In all cases antibiotics are added (penicillin 50 U/mL and streptomycin 50 μg/ml). The medium is replaced every other day. After 7 days the skin pieces are fixed in 1% neutral buffered formaldehyde, dehydrated via an ethanol-xylene series and embedded in paraffin. Sections, 10–20 μm thickness, are tinted with the use of the hematoxy-line-eosine-technique and reepithelialization is determined by light microscopy. Only total epithelialization of the wound is considered as a positive result.

On the appended drawing there is presented the result of the experiments made. In the diagram the degree of healing is recorded on the vertical axis, whereas the horizontal axis reflects the different substances and products supplied.

As is clear from the diagram of the figure the addition of 10% fetal calf serum results in complete healing after 7 days, whereas 2% fetal calf serum does not give any observable healing. Furthermore, the diagram shows that chitosan film of varying degree of deacetylation and with or without neutralization results in a certain effect by increased degree of deacetylation. Finally, the diagram through the pile furthest to the right shows that the combination of chitosan-heparin results in a healing effect largely corresponding to that obtained with 10% fetal calf serum. This effect is totally surprising and constitutes a substantial step forward within the techniques concerning healing of dermal wounds, which step forward is based on the combination of chitosan-heparin.

Example 12

Preparation of Chitosan-Heparin Films the hydrochloric salt of chitosan (5 g, 16% degree of acetylation, Pronova) is dissolved in a 2% acetic acid solution (aq. 0.5 ). The solution is autoclaved at 125° C. for 30 min. After cooling, 20 mL of the solution is added to a petridish (54 cm$^2$) and allowed to evaporate in an oven at 70° C. for 16 h. The film is neutralized with M NaOH for 3 h at room temperature and then rinsed with distilled water (3×100 mL) for 3 h each time. The resulting film is dried in an oven for 2 h at 70° C. The film is then transferred to a petridish (54 cm$^2$) and 30 mL of a sterile solution of native heparin (1% w/v, Pig mucosa, Kabivitrum) in 0.2 M phosphate buffer (pH 6.4) is added. The films are kept at room temperature over night and then rinsed with sterile water and dried in a LAF bench. Three more films are prepared as described above with the modification that they are treated with 0.5%, 0.1%, 0.01% and 0.00% solutions of heparin, respectively. The heparinized films are subjected to elemental analysis and contained 1.2%, 0.9%, 1.3%, 0.23% and 0.007% sulfur, respectively. These values correspond to a heparin content of 9.2%, 7.7%, 10.8%, 1.9% and 0%, respectively.

Example 13

Preparation of in Vitro Wounds

Figure 2:
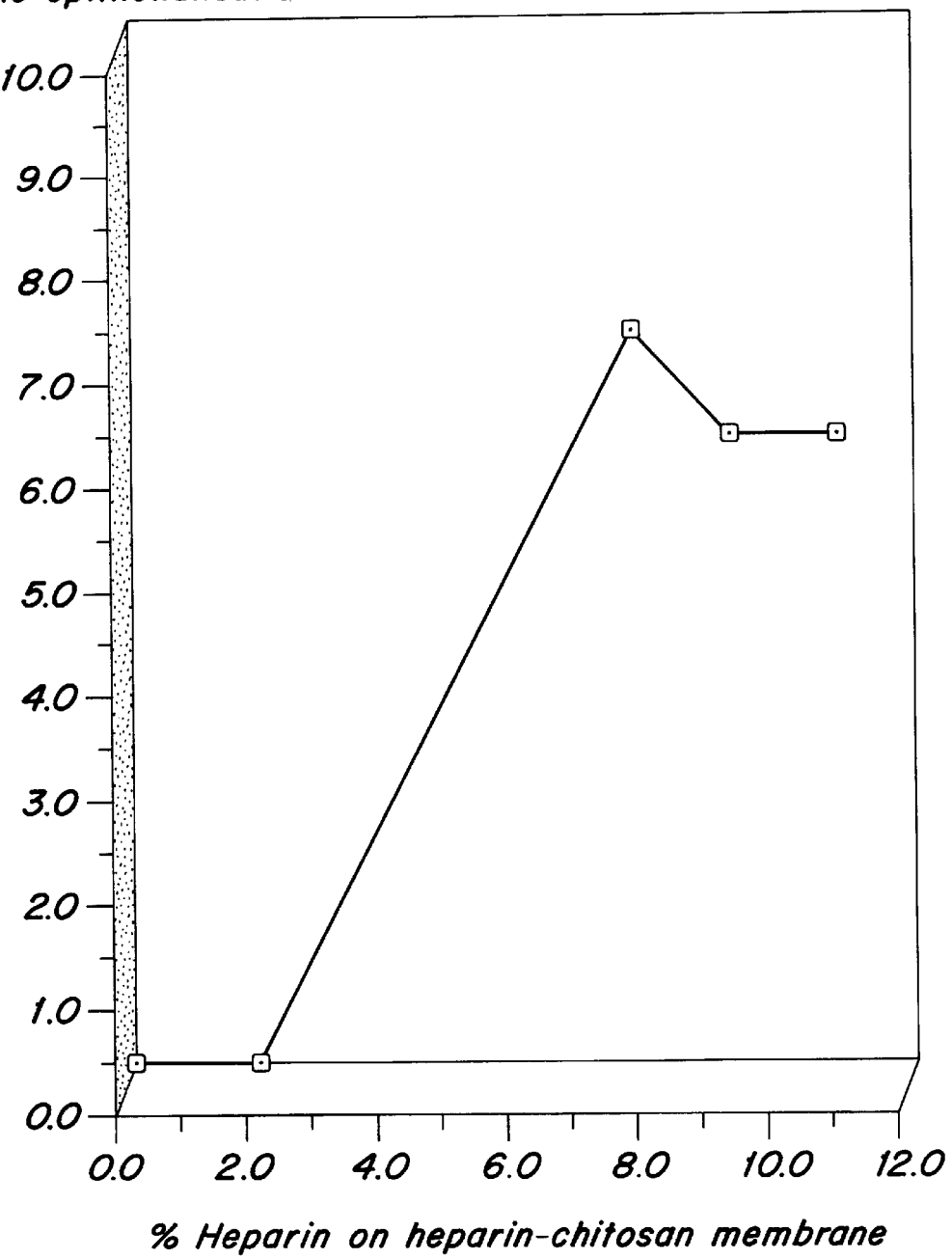
FIG. 2 is a diagram on the degree of re-epithelialisation as a function of the percentage of heparin used in heparinized chitosan membranes.

Sterile human skin is obtained from mastectomy specimens. In each experiment only skin from a single donor is used. Under sterile conditions, pieces with a diamter of 6 mm are cut with a biopsy punch (Stiefel Laboratories, UK). In the centre of each, on the epidermal side, a partial thickness wound is made with a 3 mm biopsy punch and subsequently pieces are transferred to 12-well plates (Costar) with the epidermal side up. Each well is filled with Dulbeccos Modified Eagles Medium (DMEM) to the epidermal level keeping the wound in the gas/liquid interface. Fetal calf serum, 2% (FCS) and antibiotics (penicillin 50 μg/ml and streptomycin 50 μg/mL) are added to all samples. The biopsies are divided into five groups with ten biopsies in each group. Every wound in each group is covered with a heparinized membrane, prepared as described in Example 8 above. The media are changed every day. After 7 days the pieces are fixed in 4% neutral buffered formaldehyde, dehydrated through an ethanol-xylene series and embedded in paraffin. Cross sections, 10–20 mm in thickness are stained with haematoxylin and eosin and the degree of re-epithelialization is assessed by light microscopy. Only wounds totally covered with keratinocytes are regarded as healed. As is evident from FIG. 2 films with a heparin content below about 2% do not stimulate cellproliferation in this experiment.

The invention is, of course, not restricted to the embodiments presented above and has a scope only limited by the appended claims.

We claim:

1. A method for promoting the healing of dermal wounds, which comprises applying to the site of a dermal wound a composition comprising chitosan and at least one first polysaccharide selected from the group consisting of heparin and heparan sulfate, wherein the percentage by weight of chitosan contained in said composition is substantially greater than the percentage by weight of said at least one first polysaccharide and the percentage by weight of said chitosan and said first polysaccharide are effective to promote dermal wound healing.

2. The method of claim 1 wherein said first polysaccharide is immobilized to said chitosan.

3. The method of claim 2 wherein said first polysaccharide is immobilized to said chitosan by ionic bonds.

4. The method of claim 2 wherein said first polysaccharide is immobilized to said chitosan by covalent bonds.

5. The method of claim 1 wherein the composition is in the form of a powder, an ointment, a paste, a gel, a suspension, a solution, or a film.

6. The method of claim 1 wherein the chitosan has a degree of N-acetylation which is at most about 90%.

7. The method of claim 1 wherein the chitosan has a degree of N-acetylation which is at most about 50%.

8. The method of claim 1 wherein the chitosan has a degree of N-acetylation of less than about 25%.

9. The method of claim 1 wherein said composition comprises a dermally acceptable carrier or excipient.

10. The method of claim 9 wherein the carrier or excipient comprises a viscosity-increasing second polysaccharide.

11. The method of claim 10 wherein said second polysaccharide is a cellulose derivative.

12. The method of claim 11 wherein said composition comprises an aqueous carrier.

13. The method of claim 12 wherein said first polysaccharide is present in an amount of at least about 2% by weight based on the amount of said first polysaccharide and chitosan contained in said composition.

14. The method of claim 13 wherein the amount of said first polysaccharide is at least about 4% by weight based on the amount of said first polysaccharide and chitosan contained in said composition.

15. The method of claim 13 wherein the amount of said first polysaccharide is at least about 6% by weight based on the amount of said first polysaccharide and chitosan contained in said composition.

* * * * *